(12) United States Patent  (10) Patent No.: US 8,008,068 B2
Nomura  (45) Date of Patent: Aug. 30, 2011

(54) NONHEMOLYTIC OPTICAL SENSOR WITH ENHANCED REFLECTANCE

(75) Inventor: Hiroshi Nomura, Shorewood, MN (US)

(73) Assignee: Light Pointe Medical, Inc., Eden Prairie, MN (US)

( * ) Notice: Subject to any disclaimer, the term of this patent is extended or adjusted under 35 U.S.C. 154(b) by 353 days.

(21) Appl. No.: 12/152,173

(22) Filed: May 13, 2008

(65) Prior Publication Data

US 2009/0219510 A1    Sep. 3, 2009

Related U.S. Application Data

(63) Continuation-in-part of application No. 12/072,940, filed on Feb. 29, 2008.

(51) Int. Cl.
  *C12M 1/34* (2006.01)
(52) U.S. Cl. ............... 435/288.7; 435/283.1; 435/288.4; 436/524; 436/165; 427/2.11; 427/10; 356/450
(58) Field of Classification Search ........................ None
See application file for complete search history.

(56) References Cited

U.S. PATENT DOCUMENTS

| | | |
|---|---|---|
| 5,071,248 A | 12/1991 | Tiefenthaler et al. |
| 5,122,451 A | 6/1992 | Tanaka et al. |
| 5,206,147 A | 4/1993 | Hoenes |
| 5,227,310 A | 7/1993 | Sakamoto et al. |
| 5,240,860 A | 8/1993 | Hoenes et al. |
| 5,334,508 A | 8/1994 | Hoenes |
| 5,360,827 A | 11/1994 | Toda et al. |
| 5,382,523 A | 1/1995 | Hoenes et al. |
| 5,560,781 A | 10/1996 | Banks et al. |
| 5,656,241 A | 8/1997 | Seifert et al. |
| 5,789,255 A | 8/1998 | Yu |
| 5,846,837 A | 12/1998 | Thym et al. |
| 5,859,937 A | 1/1999 | Nomura |
| 6,036,919 A | 3/2000 | Thym et al. |
| 6,045,699 A | 4/2000 | Yazawa |
| 6,157,442 A | 12/2000 | Raskas |

(Continued)

FOREIGN PATENT DOCUMENTS

JP    07-021455 B2    3/1995

(Continued)

OTHER PUBLICATIONS

R. H. Rigdon, "Hemolysis associated with plastics—a histopathologic study with polyurethane", J. Biomed. Mater. Res., vol. 4, pp. 57-71, 1970.

(Continued)

*Primary Examiner* — N. C. Yang
(74) *Attorney, Agent, or Firm* — David H. Carroll

(57) ABSTRACT

A nonhemolytic sensor for determination of analytes in erythrocyte-containing biological fluids is disclosed that comprises an optical material having a deposit on a surface thereof, where this deposit includes an analyte-reactive reagent and a particulate means for suppressing hemolysis of erythrocytes in an erythrocyte-containing biological fluid, such as whole blood. Thus, a porous array of negatively charged particles, e.g., polymeric beads having a plurality of carboxylate surface groups, are disposed on a sampling surface of an optical sensor, and suppress hemolysis of erythrocytes coming into contact with the sampling surface. In the case of an optical sensor, such particles can simultaneously enhance reflectance of a light beam transmitted through the optical material to the sampling surface site.

7 Claims, 6 Drawing Sheets

U.S. PATENT DOCUMENTS

| | | | |
|---|---|---|---|
| 6,200,773 | B1 | 3/2001 | Ouyang |
| 6,420,128 | B1 | 7/2002 | Ouyang |
| 6,455,001 | B1 | 9/2002 | Knappe et al. |
| 6,479,146 | B1 * | 11/2002 | Caruso et al. .................. 428/403 |
| 6,537,496 | B1 | 3/2003 | Knappe et al. |
| 6,586,199 | B2 | 7/2003 | Ouyang |
| 6,624,272 | B2 | 9/2003 | Futami et al. |
| 6,656,697 | B1 | 12/2003 | Ouyang |
| 6,905,653 | B1 | 6/2005 | Higuchi |
| 6,984,307 | B2 | 1/2006 | Zweig |
| 7,112,399 | B2 | 9/2006 | Dickerson et al. |
| 7,288,146 | B1 | 10/2007 | Nicolai et al. |
| 7,329,452 | B2 | 2/2008 | Clarke et al. |
| 2001/0029049 | A1 * | 10/2001 | Walt et al. ..................... 436/518 |
| 2003/0157731 | A1 * | 8/2003 | Yguerabide et al. .......... 436/523 |
| 2003/0164024 | A1 | 9/2003 | Mitsubayashi et al. |
| 2003/0170613 | A1 * | 9/2003 | Straus .............................. 435/5 |
| 2005/0123451 | A1 | 6/2005 | Nomura |
| 2005/0208543 | A1 * | 9/2005 | Vann et al. ......................... 435/6 |
| 2005/0250156 | A1 | 11/2005 | Shebuski et al. |
| 2006/0024835 | A1 * | 2/2006 | Matzinger et al. .............. 436/95 |
| 2006/0211126 | A1 | 9/2006 | Banks |
| 2006/0257558 | A1 | 11/2006 | Nomura |
| 2009/0219509 | A1 | 9/2009 | Nomura |

FOREIGN PATENT DOCUMENTS

| | | |
|---|---|---|
| JP | 10-132748 A | 5/1998 |
| JP | 10-132750 A | 5/1998 |
| WO | 2009139889 A2 | 11/2009 |

OTHER PUBLICATIONS

M.F. Dyck et al, "Lytic effects of plastic surfaces on erythrocytes", Journal of Biomedical Materials Research, vol. 5, pp. 207-223, 1971.

Banks, Bruce A. et al., Atomic Oxygen Textured Polymers, NASA Technical Memorandum 106769, Prepared for the 1995 Spring Meeting sponsored by the Materials Research Society, San Francisco, CA, Apr. 17-21, 1995, 22 pages.

International Searching Authority/KIPO, International Search Report, International Patent Application No. PCT/US2009/003004, Dec. 2, 2009, 3 pages.

International Searching Authority/KIPO, Written Opinion of the International Searching Authority, International Patent Application No. PCT/US2009/003004, Dec. 2, 2009, 6 pages.

Ishiyama, Munetaka, Topics on Chemistry: Why is the Water-Soluble Formazan Necessary?, www.dojindo.com/newsletter/review_vol 2.html#chem, undated, 7 pages, retrieved 2010.

Light Pointe Medical, Inc., Article 19 Amendment, International Patent Application No. PCT/US2009/003004, Jan. 27, 2010, 3 pages.

Nomura, Hiroshi, Reply to Office Action, U.S. Appl. No. 12/072,940, Dec. 17, 2009, 20 pages.

Nomura, Hiroshi, Supplemental Amendment, U.S. Appl. No. 12/072,940, Feb. 2, 2010, 11 pages.

Nomura, Hiroshi, Reply to Office Action, U.S. Appl. No. 12/072,940, Jul. 6, 2010, 16 pages.

Nomura, Hiroshi, Reply to Office Action, U.S. Appl. No. 12/072,940, Oct. 15, 2010, 7 pages.

Rohm & Hass, Ropaque Ultra E Opaque Polymer, Apr. 2007, 7 pages.

Simmons, E.L., Reflectance Spectroscopy: Application of the Kubelka-Munk Theory to the Rates of Photoprocesses of Powders, Applied Optics, vol. 15, No. 4, Apr. 1976, pp. 951-954.

United States Patent and Trademark Office, Office Action, U.S. Appl. No. 12/072,940, Aug. 17, 2009, 17 pages.

United States Patent and Trademark Office, Office Action, U.S. Appl. No. 12/072,940, Apr. 5, 2010, 20 pages.

United States Patent and Trademark Office, Office Action, U.S. Appl. No. 12/072,940, Aug. 17, 2010, 20 pages.

United States Patent and Trademark Office, Notice of Allowability, U.S. Appl. No. 12/072,940, Nov. 1, 2010, 6 pages.

Yasuda, H., Plasma Polymerization, Academic Press, Inc., New York, 1985, pp. 1-3, 186-189.

* cited by examiner

NONHEMOLYTIC OPTICAL SENSOR WITH ENHANCED REFLECTANCE

CROSS-REFERENCE TO PRIOR APPLICATION

This is a continuation-in-part of U.S. application Ser. No. 12/072,940, filed on Feb. 29, 2008.

BACKGROUND OF THE INVENTION

1. Field of the Invention

The present invention relates to fluid analysis, and more particularly to apparatus for body fluid analysis using optical materials.

2. Background

One method of analyzing a fluid for specific properties such as the presence and concentration of specific moieties is by analyzing changes in light directed through a surface-borne reagent to which a sample of the fluid is brought into contact. This is achieved by utilizing a reagent which produces an optically detectable physical or chemical change upon contact with one or more targeted analytes in the fluid. This method of analyzing fluids is especially effective when a colorimetric reaction is effected in the sample or on a surface in contact with the sample, wherein a color change relates to one or more specific analytes in the fluid. Such a means includes generally a specific source of light of a desired frequency tuned to the spectral range of the colorimetric reaction, and also a detector for such a light. One approach in common use is to impregnate a microporous sheet-like member with a color-producing reagent. Typically, the microporous sheet-like member is a membrane whose composition comprises a "nylon" or polyamide polymer. A fluid sample, such as of blood, is deposited on one surface of the membrane, resulting in a color change reaction with the resident reagent, and the color shade and intensity are read by means of a light beam reflected from the opposite face of the membrane. Another, increasingly contemplated, method of conducting these types of analyses is by use of optic fibers as waveguides for a light beam, both to introduce a light beam from a light source into the fluid sample and as a conduit for returning light from the fluid sample to a detector. Changes in the light beam's spectral pattern, or more often in the intensity of the beam at a specific frequency, can be correlated in some manner to the concentration of a specific analyte present in the fluid sample. Application of this concept in the field of glucose measurement in body fluids is found, for example, in U.S. Pat. No. 6,157,442. This approach customarily uses an analyte-reactive reagent or combination of reagents that undergoes a color change or develops one or more colored reaction products. Selective absorption of light at one or more frequencies associated with the spectral range of the colored reaction products occurs, resulting in measurable, (i.e., quantifiable) alterations in the light beam being accessed and evaluated by a suitable detection system. In some cases, such analyses may be based on light frequencies that occur outside the normal human range of visible light, thus entailing other than "colored" reaction products. The analyte-reactive reagent is advantageously bound or otherwise located on a surface of an optic fiber, in effect making the optic fiber into a sensor probe. For instance, an analyte-reactive reagent can be positioned on the distal tip of an optical fiber waveguide, the other end of the optic fiber being attached to an apparatus or assembly that includes a suitable detector. A suitable light source may be located extraneous to the optic fiber sensor, or brought to the fluid sample by means of the optic fiber sensor itself, or brought to the fluid sample through another optic fiber waveguide bundled with the optic fiber sensor.

Some difficulties are inherent in the use of optic fiber sensors for fluid analyses. For instance, the distal tip of an optic fiber probe presents very little surface area for attachment of an analyte-reactive reagent, resulting in a very minimal effect when assayed by means of changes in a light beam shone therethrough. Accuracy and reliability of analyses can be severely compromised by the lack of enough reagent to effect significant changes in a sensor's light beam. Another difficulty resides in designing a suitable arrangement whereby a light beam can be directed through a colored reaction product, captured by an optic fiber probe, and directed to a light detector in a reliable manner. An optimal approach would seem to be the operation of a single optic fiber probe as both the conduit for a light beam from a source into the fluid sample and the conduit for light returning from the fluid sample into the optic fiber and from thence to a suitable detection system. However, the proportion of returned light from the fluid medium adjacent the distal tip of a fiber optic waveguide is normally very poor, almost to the point of being nonexistent. When the tip is textured such as disclosed in U.S. Pat. No. 5,859,937, surface area for attachment of analyte-reactive reagents is greatly increased; also, light return is mildly enhanced by the texturing, such that a few percent of the light is recaptured by the optical fiber. Nevertheless, most of the light is lost by emanation from the surface area of the tip of even a textured tip optic fiber waveguide. The option of directing a beam of light down an optic fiber probe to a distal tip having a high surface area for disposition of a diagnostic reagent is still compromised by the loss of light signal and the minimal return of light from the distal tip through the same optic fiber to a detector.

In this regard, returned light may occur in two ways, by reflection and by reflectance. Reflected light is that portion of the light beam that, in traveling to the tip, encounters an interface between the polymer matrix and the environment (fluid sample, surface-deposited diagnostic chemistry, etc.), and which bounces back from the interface rather than crosses it. Cladding along the periphery of most optic fiber strands is designed to cause reflection of internal light beams, but no such cladding is present on a distal tip of a fiber optic probe, and a very high proportion of any light being beamed down the length of the optic fiber strand will customarily escape the confines of the optic fiber strand at that tip. Reflectance, however, refers to that portion of light that enters into a sample medium such as powder or paper, and re-emerges in the general direction of the source, where the spectral nature of the light has likely been altered by contact with the sample medium. In the present instance, the zone of analyte-reactive reagent in contact with the fluid sample represents the sample medium rather than paper or powder. The phenomenon of reflectance is treated at some length in the publication titled "Reflectance Spectroscopy: Applications of the Kubelka-Munk Theory to the Rates of Photoprocesses of Powders" by E. L. Simmons, in Applied Optics, Vol. 15, No. 4, April 1976, pages 951-954, in which also reference is made to the original publication by Kubelka and Munk in a German periodical in 1931. Such light will commonly be changed by absorption of some frequencies to varying degrees by the medium. Some patent publications loosely refer to reflectance as "reflected" light, and vice versa some patent publications refer to reflected light as "reflectance".

In the analysis of analytes by a reagent combination disposed on the tip of an optic fiber probe, the light of interest for analytical determinations is mostly lost from the tip of the optic fiber, thus requiring some means of collection of such light by apparatus external to the fiber tip. Reflectance light re-transmitted through the optic fiber from the tip is normally of such weak intensity as to greatly lower the sensitivity of the optic fiber probe in potential analytical applications. Collecting the light by means external to the optic fiber tip may overcome this difficulty but necessarily results in more complexity of design and higher cost for analytical applications, as well as introducing possible artifacts. The need exists for improved sensors wherein reflectance can be captured effectively by the fiber optic probe itself.

Similar difficulties are encountered even with sensors employing sheet-like members such as polyamides alluded to earlier in this section. When such sensors are wetted by aqueous fluid samples to be analyzed, the wetting in itself tends to make the microporous member significantly more transparent optically, and needing enhanced reflectance for optimum performance.

An additional problem encountered with these sheet-like members is the fact that the microporous polyamide membranes used for sensor construction, particularly positively charged nylon membranes (as disclosed in U.S. Pat. No. 6,420,128, which is incorporated herein in its entirety by reference thereto), are themselves hemolytic toward erythrocytes in samples of whole blood. This releases hemoglobin, which migrates far more freely through the sample matrix than erythrocytes, and generates interferences in the subsequent colorimetric analyses. In the case of some color-producing reagents—and particularly those based on tetrazolium salts—the hemoglobin can actually react with the dye system to produce color bodies, just as would blood glucose. Since the primary use of such sensors is the determination of glucose concentrations in whole blood of diabetic patients, this drawback is of major concern. One approach has been to add a porous transport layer atop the membrane to filter out erythrocytes, such as the "double-layer" embodiment disclosed in U.S. Pat. No. 5,789,255, which is incorporated herein in its entirety by reference thereto. Another approach has been to modify the color change reagent with a soluble acrylic acid polymer, also disclosed in this same reference. Nitrite salts have also been employed in tetrazolium-salt-based diagnostic strips, wherein the nitrite binds to the released hemoglobin, thus suppressing the interfering dye formation caused non-enzymatically by the hemoglobin, as disclosed in U.S. Pat. No. 6,200,773, which is incorporated herein in its entirety by reference thereto. These difficulties and subsequent approaches illustrate an ongoing need for optical sensors wherein not only enhanced reflectance is valuable, but also wherein hemolysis of erythrocytes in body fluid samples does not occur or can be reduced to such a low background level as not to develop any significant interference in the enzymatic analysis of, say, blood glucose.

SUMMARY OF THE INVENTION

It is an object of this invention, therefore, to provide a means for effectively directing an analytically useful beam of light from a light source to a sampling zone of a surface-borne analyte-reactive reagent, then capturing and directing an enhanced portion of reflectance from the sampling zone back through the same sensor toward a suitable detector, additionally providing on a sampling surface of the sensor a means to simultaneously suppress hemolysis of any erythrocytes in contact with the sensor materials.

This and other related objects, that will become apparent to one of skill in the art upon reading this disclosure, are achieved by the invention disclosed herein.

A device for determination of analytes has now been developed that comprises an optical sensor, such as a dry test strip for blood glucose analysis, having a deposit on a surface thereof, wherein this deposit includes a analyte-reactive reagent and a particulate means for enhancing reflectance of a light beam emitted through the optical material into the analyte-reactive reagent. The enhanced reflectance provides a return of light through the optical material at a level which is not only analytically useful, but involves sufficient returned light intensity so as to enable markedly improved accuracy in analytical determinations. The particulate means simultaneously suppresses hemolysis of erythrocytes in blood samples coming into contact with the sensor, thus eliminating any potentially significant interference by free hemoglobin.

A further embodiment of this device comprises a optical sensor, such as an optical fiber, having a textured surface in at least one region and further having a coating disposed on the textured surface, the coating comprising at least one analyte-reactive reagent capable of producing an optically detectable change upon reaction with at least one analyte in a sample fluid presented to the surface, wherein a means is provided for enhancing reflectance from the reagent sampling zone back into the optical guide material. The means for enhancing reflectance comprises small, inanimate, generally spherical particles having light scattering characteristics, which particles are optimally hollow, and which particles are small enough to reside within the crevices or micro-wells of a suitably textured surface, which particles simultaneously suppress hemolysis of erythrocytes that may be present in fluid samples presented to the sample receiving surface of the sensor.

A further embodiment includes a sensor comprising an optic fiber having proximal and distal ends, wherein the distal end has been textured by exposure to atomic oxygen and has subsequently been coated with a combination comprising an analyte-reactive reagent and a particulate means for enhancing reflectance into the optic fiber, wherein the analyte-reactive reagent is capable of producing an optically detectable change upon reaction with at least one analyte in a sample fluid presented to the surface of the distal tip, wherein also the proximal tip is capable of receiving light from a source coupled to the optic fiber and of directing reflectance light to a detector also coupled to the optic fiber, wherein also the particulate means simultaneously suppresses hemolysis of erythrocytes that may be present in fluid samples presented to the distal end of the sensor.

DETAILED DESCRIPTION OF THE PREFERRED EMBODIMENTS

Figure 1:
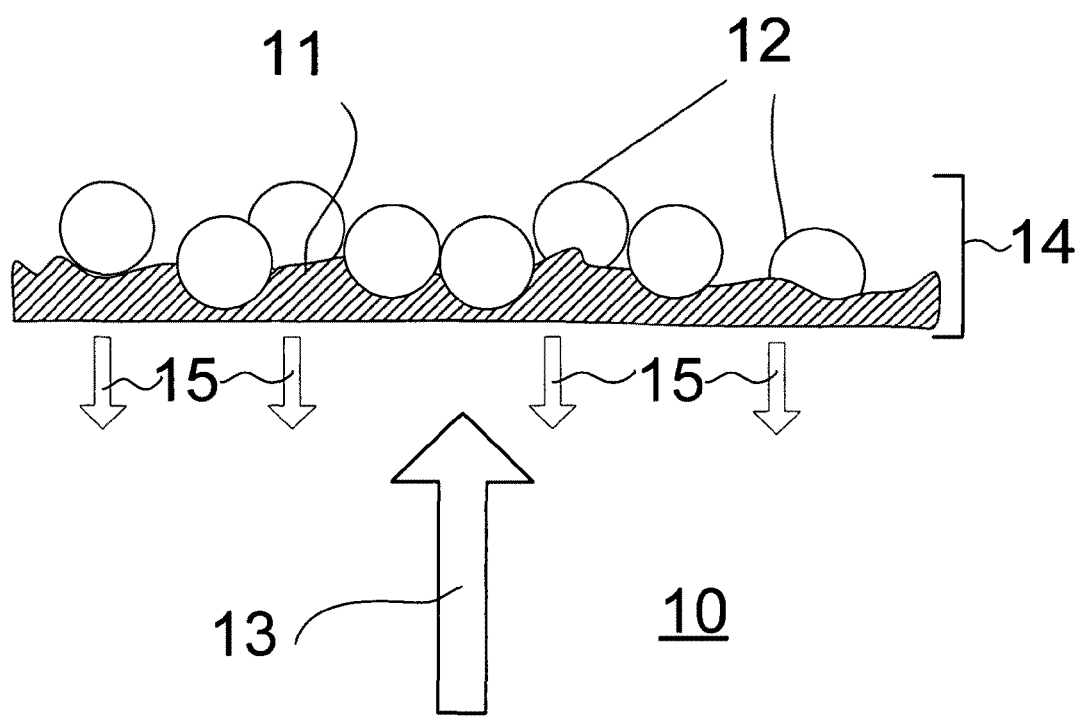
FIG. 1 is a schematic diagram of a surface coating on an optical guide material illustrating a coating combination with enhanced reflectance capability.

The present invention relates to devices and methods for analysis of aqueous samples, most notably biological fluid samples such as blood or other body fluids, particularly using optical sensor technology, including particularly optical fibers as sensor probes, but also dry test strips. While usefulness of the invention relates to various types of fluid samples of both biological and nonbiological sources, the invention disclosed herein is particularly useful with reference to whole blood, with respect to which hemolysis of erythrocytes therein causes significant interference in fluid analyses. The present invention also relates to devices optimally utilizing textured surface sites, wherein multiple advantages are achieved through increased surface area for deposition and subsequent reaction of analyte-reactive reagents and through spatial separation of cellular elements present in some types of body fluids, most particularly blood where such cellular elements include erythrocytes, leucocytes and such, but wherein hemolysis of erythrocytes may still occur through the action, for example, of tetrazolium dyes.

The present invention is an extension of an earlier invention (see cross-reference to prior application) that relates to means for enhancing the intensity of light being transmitted from a sampling zone back through the optical sensor material to a suitable detector, wherein a means for enhanced reflectance is disposed in the sampling zone, preferably in association with an analyte-reactive reagent deposited on a surface site of the optical sensor. A sample of blood or other body fluid is presented to a surface of an optical material of a sensor whereon an analyte-reactive reagent is present as a coating. The surface may be smooth, or the surface may be advantageously textured so that it presents the morphology of a field of elongated projections. The projections may be suitably spaced apart to exclude certain cellular components such as blood cells in a body fluid sample from entering into the spaces between the projections, while permitting the remaining part of the body fluid sample, which contains the analyte, to enter into those spaces. The term "analyte" is used to refer to the substance to be detected in the fluid sample. "Detected" refers to identification of the presence of a targeted analyte in the fluid sample, but most often also extends to the quantification of the targeted analyte. The phrase "analyte-reactive reagent" is defined as any reagent that can interact physically or chemically with an analyte such as to produce an optically discernible change, including changes correlative with analyte concentration in a fluid within the sampling zone.

The targeted analyte contacts an analyte-specific chemistry on the surface of the sensor, whereupon the analyte and a specific reagent interact in a manner that is optically detectable. Suitable analyte-specific chemistries may include receptor molecules as well as reactive molecules. Commonly, analyte-specific chemistries include components that generate colored species, and optical detection is based on the density and spectral nature of the colored species. In the case of blood containing cellular elements such as erythrocytes, spatial exclusion of the erythrocytes from the zone of the reagent is an important advantage of suitably textured analytical sites, when certain color development chemistries are used where the erythrocytes would interfere in such color-based assays. In commonly applied chemistries for analyzing blood sugar levels, for instance, erythrocytes often absorb light in the same general range of light frequencies in optical determinations, and must be excluded in some manner so as not to negatively influence the analytical results. The nature and arrangement of the analyte-specific chemistry varies depending on the application. For example, the analyte-specific chemistry may be a layer of one type of chemistry or an ordered array or a finely mixed composite of different types of analyte-specific chemistries. For convenience, these various options are grouped together during the remainder of this disclosure by using the term "analyte-reactive reagent". The optically detectable change may occur specifically in the coating of the analyte-reactive reagent, or in a deposit developed on the coating (such as by binding of targeted analytes), or by development of reaction products in the fluid immediately in contact with the reagent. For purposes of this disclosure, these various possibilities which each involve slightly different spatial regions are included under the term "reagent sampling zone".

A light beam of a suitable frequency or range of frequency is transmitted from the optical material into the reagent sampling zone. Changes in the spectral nature of the light beam will advantageously occur as a function of optically detectable changes in the reagent sampling zone due to interaction of the analyte-reactive reagent with an analyte in the fluid to be analyzed. The majority of this light beam is radiating in a direction away from the optical material through which the light beam was brought to the reagent sampling zone, and this outwardly radiating light does not generally reenter the optical material. In accordance with the invention herein disclosed, a means is provided for enhancing the amount of this light beam that is returned to and captured within the optical material for subsequent analysis. This means for enhanced reflectance is optimally in the form of particles that scatter light. These particles may be composed of inorganic or organic materials, organic materials referring primarily to synthetic polymers. Inorganic particles useful as reflectance enhancing agents include silicates and related glasses, and may be in the shape of beads or similarly spheroidal shapes. They may be solid or hollow. Organic particles useful as reflectance enhancing agents will include polymers of various compositions, and may also be solid or hollow. Hollow beads are particularly effective. In that the analyte-reactive reagent must be accessed by the fluid sample, these reflectance enhancing particles are desirably not film-forming, meaning that a coating or array of these particles will not form a film impenetrable to fluid transport. These particles are to be associated with an analyte-reactive reagent coating, preferably by co-deposition as a mixed coating on the surface of an optical material, so as to be present in the reagent sampling zone. In practice, the analyte-reactive reagent will be present as a coating intimately in contact with a surface of the optical material and the suitable reflectance enhancing particles will be in contact with the reagent layer but optimally will extend beyond the reagent layer spatially. Thus, in a preferred configuration, a majority of the analyte-reactive reagent will be advantageously sandwiched between the optical material and the reflectance enhancing particles. A particularly effective arrangement is a textured surface on an optic material wherein both the analyte-reactive reagent and the reflectance enhancing particles are deposited within valleys or crevices of the surface.

The reflectance enhancing particles are normally to be applied to the surface of an optical material from an aqueous dispersion. The particles may be co-deposited on the surface along with the analyte-reactive reagent in a single step. Alternatively, the particles may be deposited in a separate step, preferably after first depositing a coating of the reagent. Drying of the coating or coatings at some point in the process so as to present a dry sensor for handling and storage accomplished. FIG. 1 shows a schematic representation of a surface coating on an optical guide material illustrating a coating combination with enhanced reflectance capability. The optical material 10 has on a surface thereof a coating 11 containing an analyte-reactive reagent. Embedded in this coating and extending outward therefrom are a plurality of reflectance enhancing particles 12. A beam of light, whose direction is indicated by the arrow 13 is transmitted through the optical material 10 into the coating 11. A portion of this light, having traveled into the reagent sampling zone (indicated by the bracket 14) is redirected back into the optical material, as indicated by the arrows 15. In practice, a fluid sample to be analyzed will be presented to and will bathe the reagent sampling zone, including immersion of the reflectance enhancing particles.

Particles with optimal reflectance enhancing characteristics will have a refractive index significantly different from water (refractive index=1.333) or aqueous fluid samples (refractive index typically slightly above 1.333). Divergences in refractive index from 1.000 will generally result in greater light scattering by the particles at greater divergences, and thereby greater reflectances. Polytetrafluoroethylene (PTFE) has a refractive index if 1.35, which is inconveniently close to the index of refraction of water and provides minimal reflectance enhancement. Silicate glass particles typically have a refractive index of about 1.47, which is sufficiently different from 1.333 as to provide some enhancement of light reflectance. Diatomaceous earth such as Celatom (trademark of Eagle Picher Industries) has been used in blood glucose test strips, but tends to "go clear", i.e., become optically transparent to visible light, when immersed in aqueous media, such as to not provide useful reflectance enhancement, due to the closeness of its index of refraction to that of water. Most polymeric materials have refractive indices in the range of 1.49 to 1.65, and serve well in enhancing reflectance, with optimal results being obtained at the higher index values. Hollow particles having air or other gas in the hollow interior possess an additional advantage, in that the refractive index of air, for example, is 1.000, which augments the scattering of any light entering into the hollow particles. Thus, hollow particles composed even of glass of PTFE may suitably enhance light reflectance in aqueous media in a reagent sampling zone. However, in the invention as disclosed herein, hollow particles of synthetic polymer materials having air within the hollow cavities are most preferred, being generally the most effective in light scattering characteristics and reflectance enhancements. Coatings comprising analyte-reactive reagents combined with reflectance enhancing particles are preferably no more than 10 microns (μm) in thickness, more preferably no more than 5 μm in thickness, and most preferably are in the range of 2 μm in thickness. Wherein textured surfaces are employed, coatings in the range of 2 microns or less in thickness are particularly suitable for deposition within the crevices or valleys of the textured surface morphology.

A sensor of the present invention disclosure will include an optical material through which light is intended to be transmitted. The optical material may be in sheet form, fiber form, or in other suitably shaped forms. A particularly suitable optical material is the type of light wave guide commonly referred to as an optical fiber. The optical fiber may be a single optical fiber, or may be a bundle of optical fibers. A minimally invasive sensing device that uses a light conducting fiber having a localized textured site thereon and methods for its manufacture and use are described in U.S. Pat. No. 5,859,937, which issued Jan. 12, 1999, to Nomura, and which is incorporated herein in its entirety by reference thereto. Optical fibers may be fabricated from a variety of polymers or plastics such as polymethylmethacrylate (PMMA), polycarbonate, polysulfones, polyamide, polystyrene, polyimide, polyvinyl chloride (PVC), and from other types of optical materials such as glass, plastic, glass/glass composite and glass/plastic composite fiber waveguides. Optical fibers typically although not necessarily are provided with a cladding to support the fiber and assist in guiding light along the fiber. Prior to texturing, the fiber tip is given a desired geometric shape, which is dependent on the application and performance requirements, and which include planar surfaces either normal with respect to or otherwise angled with respect to the fiber axis, convex and concave conical surfaces, and convex and concave semi-spherical surfaces.

A textured surface may be provided on a variety of optical materials other than fibers. Another type of sensor element is made from a sheet of transparent optical material such as, for example, a polymer or plastic (including polycarbonate and polyimide), glass, and quartz. If sample receiving areas are desired in the sheet, they may be formed by any of various processes depending on the type of optical material. Where the material is quartz, for example, the sample areas may be etched using dry or wet etch processes. Where the material is a molded plastic, the mold may contain certain surface recesses and protrusions for forming the sample areas. The sheets may include other optical components such as lenses. Multiple sensor elements may be made from each sheet by dicing, laser cutting, stamping, or otherwise dividing the sheet. Individual sensor elements or entire sheets or parts of sheets may be incorporated into a variety of sensing instruments having a diversity of different applications.

While various surface texturing processes are available, plastic optical materials preferably are textured by etching with atomic oxygen. Generation of atomic oxygen can be accomplished by several known methods, including radiofrequency, microwave, and direct current discharges through oxygen or mixtures of oxygen with other gases. Directed beams of oxygen, such as by an electron resonance plasma beam source, may also be utilized, as set forth in U.S. Pat. No. 5,560,781, issued Oct. 1, 1996 to Banks et al., which is incorporated herein in its entirety by reference thereto. Techniques for surface texturing are described in the aforementioned U.S. Pat. No. 5,859,937, previously incorporated herein by reference thereto.

Atomic oxygen can be used to microscopically alter the surface morphology of polymeric or plastic materials in space or in ground laboratory facilities. For polymeric or plastic materials whose sole oxidation products are volatile species, directed atomic oxygen reactions produce surfaces of microscopic cones. However, isotropic atomic oxygen exposure results in polymer surfaces covered with lower aspect ratio sharp-edged craters. Isotropic atomic oxygen plasma exposure of polymers typically causes a significant decrease in water contact angle as well as altered coefficient of static friction. Atomic oxygen texturing of polymers is further disclosed and the results of atomic oxygen plasma exposure of thirty-three (33) different polymers, including typical morphology changes, effects on water contact angle, and coefficient of static friction, are presented in Banks et al., "Atomic Oxygen Textured Polymers", NASA Technical Memorandum 106769, Prepared for the 1995 Spring Meeting of the Materials Research Society, San Francisco, Calif., Apr. 17-21, 1995, which hereby is incorporated herein in its entirety by reference thereto.

The general shape of the projections in any particular field is dependent upon the particulars of the method used to form them and on subsequent treatments applied to them. Suitable projection shapes include, for instance, conical, ridge-like, pillared, box-like, and spike-like. While the projections may be arrayed in a uniform or ordered manner or may be randomly distributed, the distribution of the spacings between the projections preferably is fairly narrow with the average spacing being such as to exclude certain cellular components of blood, such as the red and white blood cells, from moving into the space between the projections. The projections function to separate blood components so that the analyte that reacts with the surface-resident agent on the biosensor substrate is free of certain undesirable body fluid components. Most particularly preferred texturing is as disclosed in U.S. Published Patent Application 2006/0211126 by Bruce A. Banks, published Sep. 21, 2006, which is herein incorporated in its entirety by reference thereto, wherein polymer surfaces are exposed to a directed beam of energetic oxygen atoms or ions, these atoms or ions having isotropic energy levels greater than 1 eV, preferably in the range of 50 to 100 eV, and were referred to therein as being hyperthermal. Atomic oxygen texturing is discussed also in applications filed previously, titled Plasma Polymerization of Atomically Modified Surfaces (Published Application No. 2006/0257558), and System and Apparatus for Body Fluid Analysis Using Surface Textured Optical Materials (Published Application No. 2005/0123451), both listing inventor Hiroshi Nomura of Shorewood, Minn., which are incorporated herein by reference in their entirety. As a result of atomic oxygen texturing of the optical fiber or other optical material, the surface of the optical fiber/material includes a plurality of elongated projections. The optical material may include one, two, or more surface textured areas. The tip of the fiber may be textured, as well as the end of the optical fiber. The atomic surface texturing of optical materials is believed to improve sensitivity and provide an increased effective sensing area and limit background noise by supporting multiple ray reflections responsive to the light-influencing property of the analyte-specific chemistry.

The projections are suitably spaced apart to exclude certain cellular components, such as red and white blood cells, of the body fluid sample, such as blood, from entering into the micro-wells or valleys between the projections, while permitting the remaining part of the body fluid sample, such as plasma, which contains the analyte, to enter into those wells or valleys. This is particularly preferred in blood glucose determinations. Analytes/biomarkers in the blood plasma, which are indicative of cellular and/or soluble platelet activation and coagulation activation, contacts or associates with the analyte specific chemistries on the surface of the elongated projections, whereupon the analyte and the analyte specific chemistry interact in a manner that is optically detectable. This permits almost instantaneous analysis of the available plasma component of blood.

For some applications, the atomic oxygen textured surface on the optical guide material may be advantageously modified by plasma polymerization to allow for the adherence of the analyte specific chemistries specific for the desired analyte to be assayed. If there is more than one textured surface, one or more of the textured surfaces may be modified by plasma polymerization. Plasma polymerization and treatment are processes to modify the surface of substrate materials to achieve specific functionality. Such surfaces may be modified to become wettable, non-fouling, slippery, crosslinked, reactive, reactable and/or catalytic. The plasma polymerization process is a chemical bonding technology in which a gaseous plasma is created at or near ambient temperatures in a modest vacuum, causing a gaseous monomer to chemically modify the surface of a substrate material. The modification of surfaces by gaseous plasmas in this manner is treated at length in the book titled "Plasma Polymerization" by H. Yasuda [Academic Press, New York, 1985, ISBN 0-12-768760-2].

In biosensor applications, affinitive materials can be prepared by plasma polymerization techniques. The development of bio-affinitive materials involves the selection of base materials, covalent coupling chemistry, and ligands. One feature of a plasma polymerization surface-modified composite sensor is its high reactivity and specific selectivity. It is standard practice to perform a blood analysis to separate plasma from whole blood via filtration techniques. This use of plasma eliminates common problems encountered when red and white blood cells are present in the sample, namely, optical interference (light absorption and light scattering) and plasma volume displacement. The resulting measurement can be significantly different from those obtained directly on whole blood.

Figure 2:
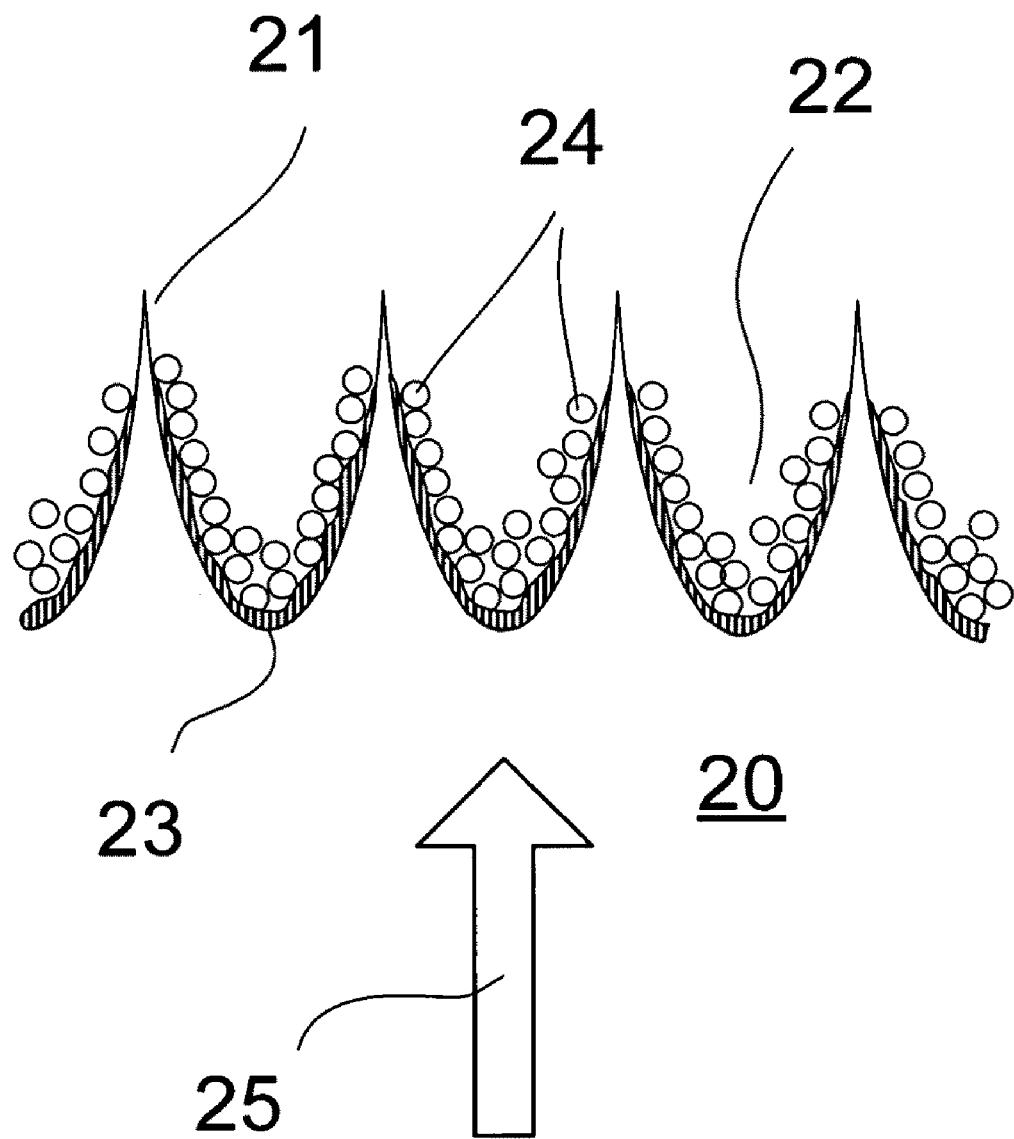
FIG. 2 is a schematic diagram of a textured surface of an optical guide material illustrating a coating combination with enhanced reflectance capability.

FIG. 2 sets forth a schematic representation of one embodiment of the invention. A series of peaks and valleys achieved by means of atomic oxygen texturing are displayed, wherein an array of projections 21 (peaks) and micro-wells 22 (valleys) are present on the surface of and optical material 20. A deposit is present within the micro-wells which includes a coating 23 of an analyte-reactive reagent in admixture with light scattering particles 24. In operation, a light beam would travel through the optical material in the direction indicated by the arrow 25, and exit the optical material into the reagent sampling zone present within the micro-wells. Reflectance from the reagent sampling zone would reenter the optical material and be transmitted in a direction through the optical material generally opposite to the arrow 25. Reflectance would be enhanced due to the presence of the light scattering particles 24, which serve to re-direct the path of light incident upon them. Much of this light would otherwise continue in a direction away from the matrix of the optical guide material 20, much of it generally continuing in the same direction indicated previously by the arrow 25. The light scattering particles are optimally small enough to fit within the micro-wells, and further are advantageously held in place by one or more binder materials used in preparing a coating of the analyte-reactive reagent although, as will be seen later with Example 1 and associated Table 1, a binder isn't always needed. Appropriate examples of such binders are water-soluble or water-dispersible polymers such as polyacrylic acid and polyacrylamide. Preferred binders will be polymeric in nature and, in most cases, readily wetted by aqueous media. The optimal binder will be usually selected on the basis of its compatibility with the specific chemistry of a chosen analyte-reactive reagent, and this is well within the capability of one of normal skill in the art, since the immobilization of the light scattering particles along the surfaces of the micro-wells is rather easy to accomplish.

Suitable light scattering particles preferably are of such dimensions as to fit within the wells between the elongated projections, but larger dimensions may be accommodated within the scope of this invention such that the light scattering particles are excluded from the wells in the same manner as blood cellular components. It is preferable, however, that the dimensions of the light scattering particles allow such particles to fit into and reside within the wells of the textured surface. Suitable light scattering particles may be polymeric in nature or may be fashioned from inorganic matter. One example of a light scattering material particularly effective in this invention is an opaqueness-generating polymer, in emulsion form, consisting of spherical styrene-acrylic beads, available from Rohm & Haas Co. under the tradename Ropaque™. The intended purpose of these beads is as an opacifying agent in paint films, in that they provide high hiding power. These beads are hollow, and are customarily supplied as aqueous emulsions wherein the cavities within the beads are water-filled. During drying of these beads, water permanently diffuses from the hollow interiors, resulting in encapsulated air voids. The hollow beads, in the dry state, exhibit highly effective light scattering characteristics, which results in their utility as opacifying agents. In addition, these particles preferably do not effectively form impenetrable or impermeable films under conditions of usage herein, so that fluid from a body fluid sample can still enter and bathe the surfaces of the textured site. In practice, the textured site is treated impregnated with an analyte-reactive reagent plus the light scattering particles in such a manner as to replace the water inside the hollow particles with a gaseous medium such as air, such as by means of a drying step.

While the foregoing discloses both a means for enhancing reflectance in optical sensors and also the benefit of surface texturing when the optical sensors are in the form of optical fibers having the sensing element on a tips thereof, hemolysis is a complicating factor when the sensor is in the form of a dry test strip employing a sheet-like microporous "nylon" member, or when the sensor in either format (dry test strip or optical fiber) employs tetrazolium dyes for assay of blood components such as glucose. Both the microporous "nylon" members and the tetrazolium dyes have been implicated with hemolysis. It is now herein disclosed that certain types of light reflectance enhancement particles also can be selected that simultaneously suppress hemolysis. Particularly preferred are particles that have a weak negative surface charge. While the invention is not to be bound by the following theory, it is believed that positively charged surfaces and/or positively charged analyte-reactive reagents interact destructively with the cell membranes of erythrocytes, causing cell membrane disruption and leakage of otherwise contained hemoglobin into the sampling zone. A non-film-forming surface array of these negatively charged particles effectively shields the erythrocytes from the membrane-disrupting effects of the aforementioned hemolytic reagents. Of particular effectiveness in this invention are Ropaque™ hollow particles, which are known to have a plurality of surface-borne carboxylate groups. Other negatively charged groups may be pendant on the particle surfaces in place of carboxylate groups, including for example sulfonate, sulfinate, phosphate, and phosphate groups. Combinations of such groups may be present on the surface of such particles. But the weakly anionic nature of carboxylate groups are sufficient and effective in the present invention. The following examples illustrate the salutary effects of negatively charged particles, such as Ropaque, in both enhanced reflectance and in suppressing hemolysis in whole blood deposited on "nylon" membranes such as used in dry test strips.

EXAMPLE 1

The following example illustrates the applicability of this invention in enhancing reflectance. Optic fibers of 2 mm in diameter, having tips textured with atomic oxygen in accordance with the method published by Bruce A. Banks in U.S. Published Patent Application 2006/0211126, were treated with 2 microliters of an aqueous reagent containing Ropaque™ Ultra Emulsion (30 solid weight %) diluted by volume to varied concentrations from zero to 10 volume percent, followed by drying. No binder needed to be added to the diluted emulsion, in that the Ropaque beads showed sufficient natural adhesion to the textured surface so as to remain in place. A beam of light was directed through the optic fibers toward the textured tips, and light reflectances at 635 nm were measured and compared both with the tips dry and the tips immersed in whole blood containing 100 mg/dl glucose. Results are shown in Table 1, wherein data are expressed in Relative Light Units (RLU). The data in Table 1 show greatly increased light reflectance due to the presence of Ropaque™ opacifying particles disposed on the textured optic fiber tips. It can be seen from the data in Table 1 that reflectance could be enhanced by as much as 450% (with whole blood) to as high as 650% in a dry state.

TABLE 1

Reflectance Enhancement with Ropaque ™ at Varied Concentrations

| Ropaque Concentration (vol %) | Light Reflectance (635 nm) Dry (RLU) | Light Reflectance (635 nm) with Whole Blood (RLU) |
|---|---|---|
| 0 | 200 | 142 |
| 1 | 900 | 440 |
| 5 | 1215 | 667 |
| 10 | 1317 | 634 |

EXAMPLE 2

Figure 3:
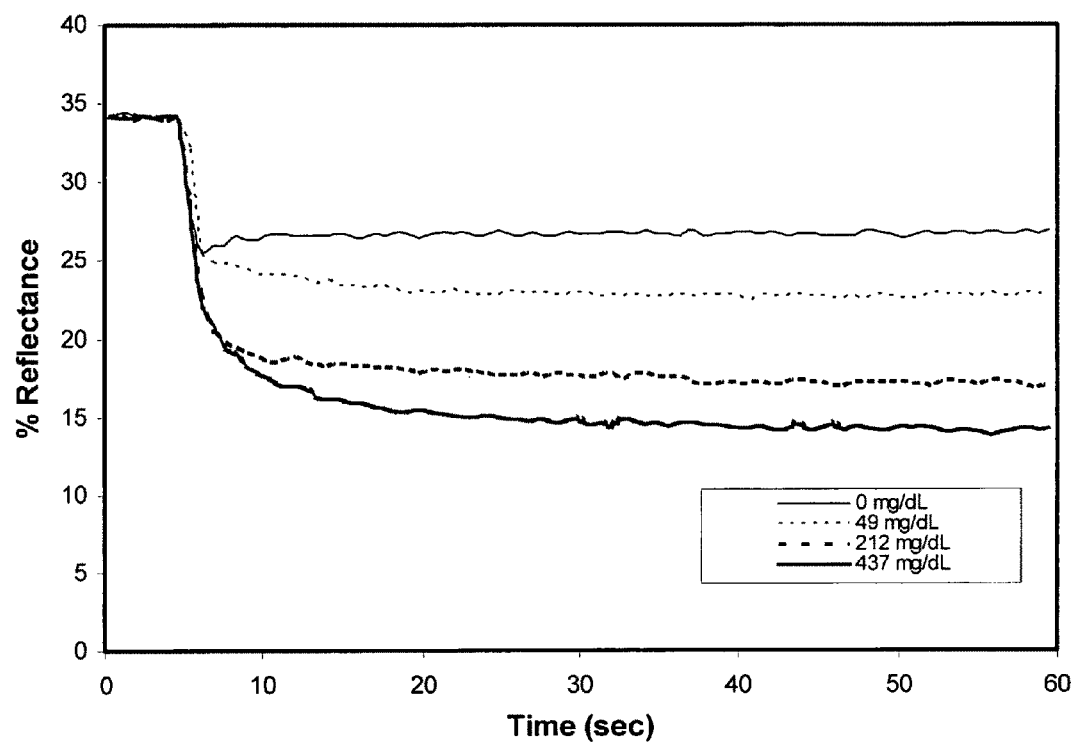
FIG. 3 is a graph of percent reflectance of 635 nm light as a function of time at various blood glucose concentrations with reflectance enhancement.
Figure 4:
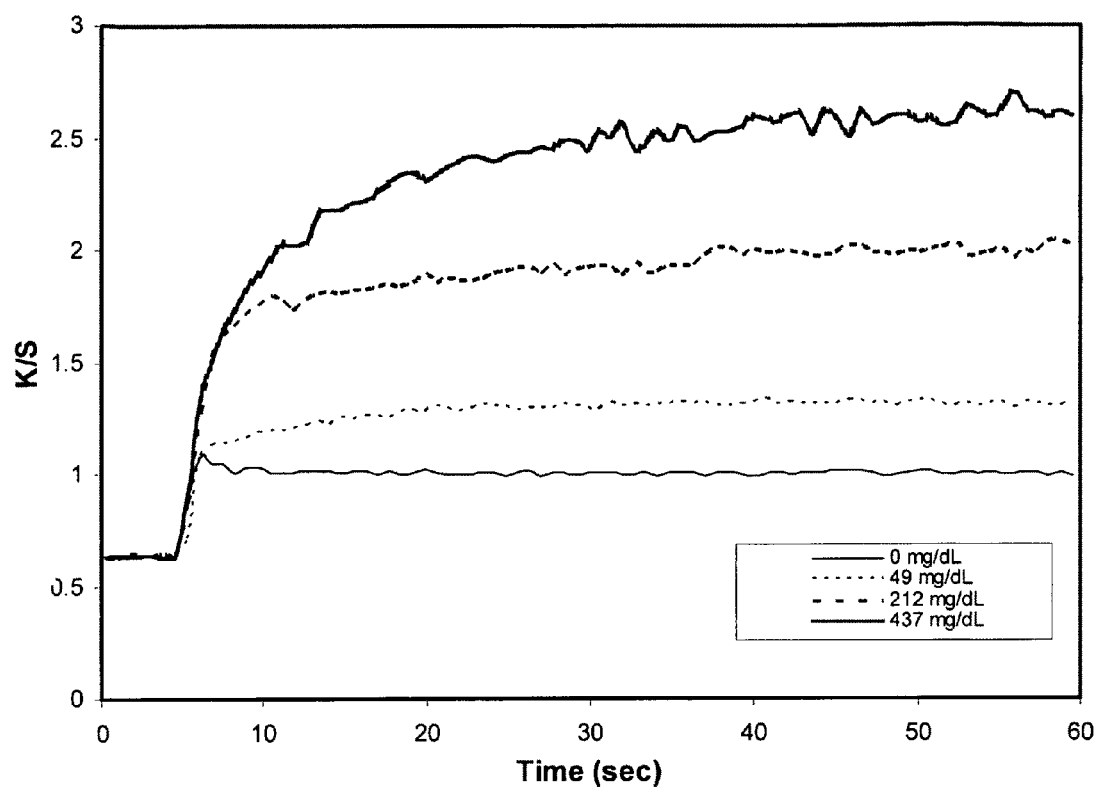
FIG. 4 is a graph of K/S calculated as a function of time for various blood glucose concentrations with reflectance enhancement.

Optic fibers 2 mm in diameter having tips textured with atomic oxygen were treated with 1 microliter of a reagent blend for blood sugar analysis containing 16 mM MES [2-morpholinoethanesulfonic acid, monohydrate], 6 mM calcium chloride, 4 mM methoxy PMS [1-Methoxy-5-methylphenazinum methylsulfate, obtained from Dojindo Co, Japan], 1800 U/ml PQQ-dependent GDH [pyrroloquinolin-quinone 1-oxidoreductase-dependent glucose dehydrogenase, obtained from Amano Enzyme Inc., Japan], 14.8 mg/dl WST-5 [2,2'-Dibenzothiazolyl-5,5'-bis{4-di(2-sulfoethyl)carbamoylphenyl}-3,3'-(3,3'-dimethoxy-4,4'-biphenylene) ditetrazolium, disodium salt], 0.125 wt % poly(acrylic acid) [partial sodium salt solution, MW ca. 5,000, obtained from Sigma-Aldrich Chemical Co.] and 2 vol % Ropaque™ Ultra Emulsion. The treated fibers were then dried for 5 minutes at 50° C. Dried, coated fibers were stored covered at room temperature until testing. In testing, whole blood standards were prepared having one of four different glucose levels. Fibers were mounted in an optical detector and light reflectance testing was initiated. After an initialization period of approximately 3 seconds, each optic fiber tip was contacted with an amount of the whole blood (hematocrit 40%) equaling 0.5 μl, one for each glucose concentration level at 0, 49, 212, and 437 mg/dl. FIG. 3 shows a graph of the tracings of percent reflection of a 635 nm light beam obtained at each of the four glucose concentration levels. The tracings showed stable development of light reflectance signals easily readable by the light sensor apparatus. K/S (Kebulka-Munk absorption parameter) values were also calculated and plotted versus time for these four whole blood glucose concentrations, and the results are displayed in the graph in FIG. 4. This example demonstrates the utility of the present invention disclosed herein.

COMPARATIVE EXAMPLE A

Figure 5:
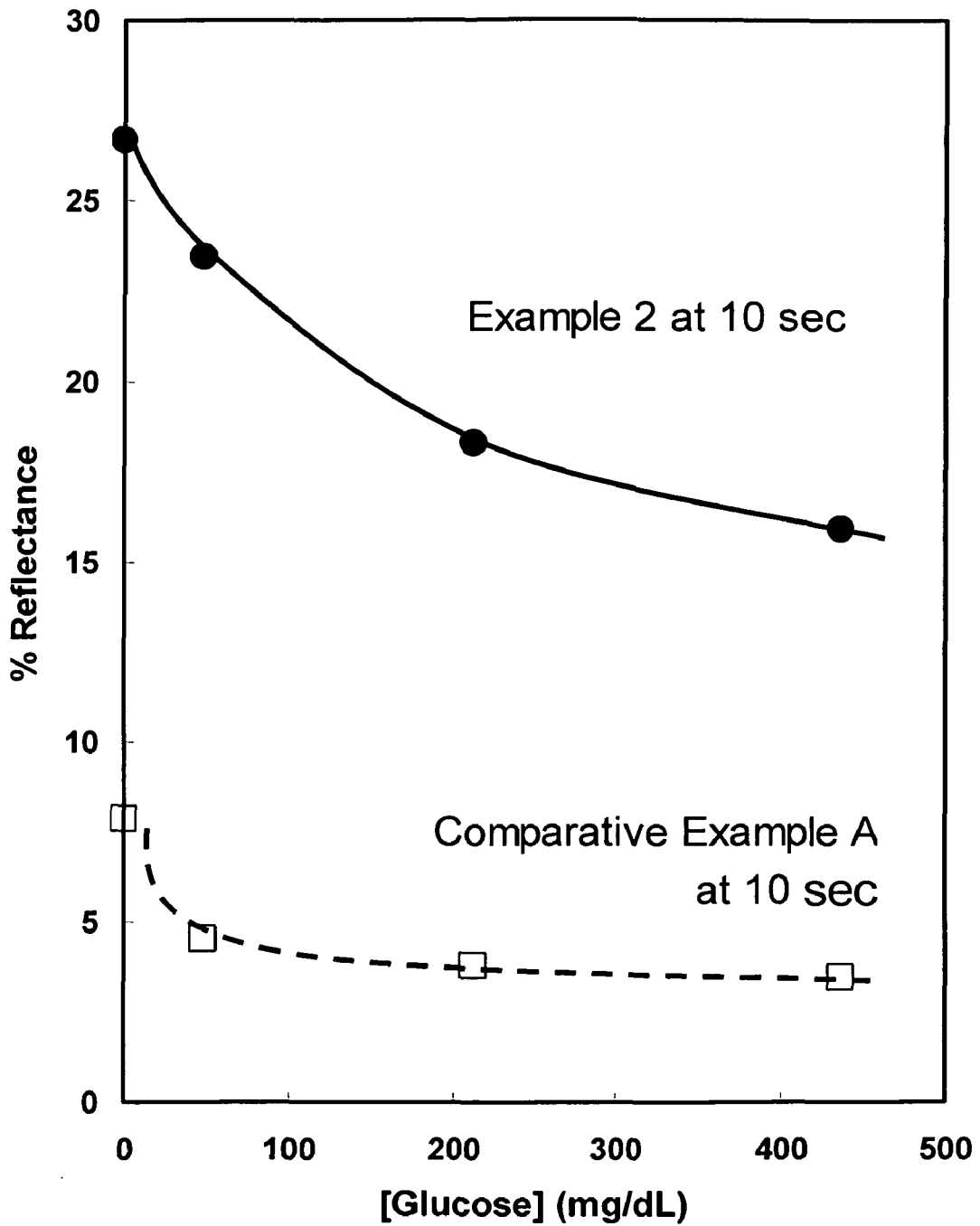
FIG. 5 is a graph of percent reflectance as a function of blood glucose concentrations with and without enhanced reflectance capability.

Optic fibers of 2 mm in diameter having tips textured with atomic oxygen were treated with 1 microliter of a reagent blend for blood sugar analysis containing 16 mM MES, 6 mM calcium chloride, 4 mM methoxy PMS, 1800 U/ml PQQ-dependent GDH, and 14.8 mg/dl WST-5. No reflectance enhancing particles were provided in the recipe. Fibers were dried for 5 minutes at 50 C. Dried, coated fibers were stored covered at room temperature until testing. In this example, 0.5 microliter of whole blood (HCT 40%) was added after an initial waiting period of approximately 3 seconds. FIG. 5 shows the percent reflectance at 10 seconds and at different glucose concentrations (lower curve), along with comparison data taken from Example 2 at 10 seconds (upper curve). Reflectances were in the range of 3 to 4%, compared to reflectances of about 15 to 25% in the presence of Ropaque™ particles, the latter representing at least a fourfold increase in light reflectance compared to the former. The result showed that there was a very small percent reflectance change depending on glucose concentration (lower curve), with insufficient differentiation to determine glucose concentration in blood with any reliability. Without reflectance enhancement, most of the lower curve approximated a plateau in the region of interest.

EXAMPLE 3

Figure 6:
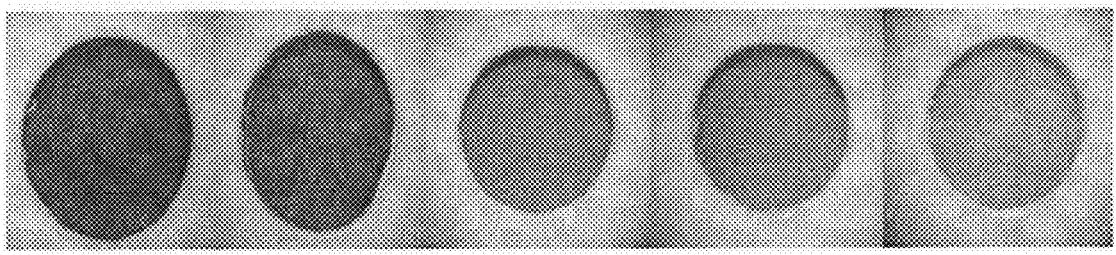
FIG. 6 is a photograph (in black and white) of hemolysis per Example 3.

A single-layer reinforced nylon microporous membrane, available commercially from Cuno Corporation, USA, under the designation BLA080, was used in this and the following example. The nylon membrane had an asymmetric structure, the more-open side having a 2.5 μm nominal pore size and the tighter side having a 0.8 μm nominal pore size. The reagent composition as used above in Example 2 was applied to the more open side of the nylon membrane in this example, along with varying amounts of Ropaque™ particles (i.e., 30 solid wt % Ropaque™ Ultra Emulsion added at 0, 2.5, 5, 7.5 and 10% by volume to the tetrazolium reagent composition of Example 2). The treated membranes were then dried. In this application, the suspended particles remain adsorbed on the original surface of application, and a substantial portion of the analyte-reactive reagent chemicals migrate to the tighter side of the membrane. Whole Droplets of whole blood without glucose (0 mg/dl) were applied to the more open side of the membranes. Hemoglobin permeation through the membrane, indicative of hemolysis, was easily observed with the 0% Ropaque condition, and to a minor extent for the 2.5% Ropaque condition, looking at the tighter side (the underside) of the membranes. At 0% Ropaque, the color of the underside changed from white to red. At 2.5% Ropaque, color changed from white to pink. Color change was nearly absent at higher Ropaque concentrations. This color development was readily within less than 10 seconds after blood was applied. After 10 seconds, a photograph was taken to visually compare the color change (white to red/pink) on the underside (see FIG. 6). The intensity of the color at 635 nm, reflectance mode, was measured by spectroscopy using an instrument manufactured by Ocean Optic Inc., USA, and results are listed in Table 2.

TABLE 2

Red Color (Hemoglobin) Density Relative to Ropaque ™ Concentration

| Ropaque Concentration (vol %) | Light Reflectance at 630 nm (%) |
|---|---|
| 0 | 52.7 |
| 2 | 55.2 |
| 5 | 71.9 |
| 7.5 | 80.2 |
| 10 | 81.0 |

In this example, concentrations of Ropaque at higher than 5% applied to the nylon membrane surface achieved essentially full suppression of hemolysis that would otherwise have occurred by the combined effects of the nylon membrane surface and the tetrazolium dye. Later, at approximately 5 minutes after application of the blood droplets, tetrazolium dye reaction with the hemoglobin was observable, being decidedly pronounced in the 0% Ropaque condition, was present to a minor extent in the 2.5% Ropaque condition, and at generally baseline values in the other conditions, as observed approximately 5 minutes after blood application.

Thus, the utility of these weakly negatively-charged particles in suppressing erythrocyte hemolysis, when dispersed on the surface of an optical sensor, has been discovered and is herein disclosed in the present invention. Applicability of the hemolysis-suppressing particles includes both sheet-like and optical-fiber-type sensors, as well as both textured and non-textured surfaces. The present invention, therefore, should not be considered limited to the particular examples described above, but rather should be understood to cover all aspects of the invention fairly set out in the attached claims. Various modifications and equivalencies may be readily apparent to those of skill in the art to which the present invention is directed, upon review of the present specification. The claims are intended to cover such modifications and equivalencies.

The invention claimed is:

1. A sensor for measuring concentration of an analyte in an erythrocyte-containing biological fluid comprising:
   an optical material having a surface site wherein the surface site of the optical material presents a textured field of projections and micro-wells, the projections being spaced apart for excluding the erythrocytes from entering into the micro-wells; and
   a deposit disposed on the surface site of the optical material for contacting the biological fluid, the deposit being disposed in each of the micro-wells and comprising an analyte-reactive reagent and an array of spherical styrene-acrylic beads penetrable to transport of the biological fluid exclusive of the erythrocytes contained therein.

2. The sensor of claim 1 wherein:
   the optical material comprises an optical fiber; and
   the surface site is upon a distal tip of the optical fiber.

3. The sensor of claim 1 wherein:
   the body of optical material comprises an optical fiber; and
   the surface site is upon a sidewall of the optical fiber.

4. The sensor of claim 1 wherein:
   the body of optical material comprises a sheet of optical material; and
   the surface site is upon a major surface of the sheet.

5. The sensor of claim 1 wherein the analyte-reactive reagent in each of the micro-wells comprises a tetrazolium dye reagent for blood glucose determination.

6. The sensor of claim 1 wherein the beads are hollow.

7. The sensor of claim 1 wherein the analyte-reactive reagent is disposed as a layer intimately in contact with the surface site of the optical material, the array of beads being in contact with the reagent layer and extending beyond the reagent layer spatially with a majority of the analyte-reactive reagent being sandwiched between the optical material and the array of beads.

* * * * *